United States Patent [19]

Sanders

[11] Patent Number: 5,554,194
[45] Date of Patent: Sep. 10, 1996

[54] MODULAR SURGICAL IMPLANT

[75] Inventor: Deborah L. Sanders, West Chester, Pa.

[73] Assignee: United States Surgical Corporation, Norwalk, Conn.

[21] Appl. No.: 480,086

[22] Filed: Jun. 7, 1995

[51] Int. Cl.⁶ .............................. A61F 2/28; F16B 12/44
[52] U.S. Cl. .................. 623/16; 623/18; 403/65; 403/76; 403/141
[58] Field of Search .................. 623/17, 16, 18, 623/48, 15; 63/DIG. 3; 606/71; 403/65, 66, 76, 141

[56] References Cited

U.S. PATENT DOCUMENTS

| | | | |
|---|---|---|---|
| 2,947,053 | 8/1960 | Sanderson | 63/DIG. 3 |
| 3,488,779 | 1/1970 | Christensen | 623/48 |
| 3,506,982 | 4/1970 | Steffee . | |
| 3,638,243 | 2/1972 | Campbell, Jr. et al. . | |
| 3,837,008 | 9/1974 | Bahler et al. . | |
| 3,879,766 | 4/1975 | Lowe et al. . | |
| 4,044,725 | 8/1977 | Miller | 63/DIG. 3 |
| 4,306,320 | 12/1981 | Delp | 623/48 |
| 4,636,218 | 1/1987 | Fukuura et al. | 623/16 |
| 4,770,008 | 9/1988 | Yamaura | 63/DIG. 3 |
| 4,883,492 | 11/1989 | Frey et al. . | |
| 4,892,548 | 1/1990 | Niederer et al. . | |
| 4,990,161 | 2/1991 | Kampner . | |
| 5,011,497 | 4/1991 | Persson et al. | 623/18 |
| 5,108,437 | 4/1992 | Kenna . | |
| 5,133,761 | 7/1992 | Krouskop . | |
| 5,246,458 | 3/1993 | Graham | 623/17 |
| 5,290,314 | 3/1994 | Koch et al. | 623/18 |
| 5,458,647 | 10/1995 | Brochier et al. | 623/18 |

FOREIGN PATENT DOCUMENTS

| | | | |
|---|---|---|---|
| 518278 | 12/1992 | European Pat. Off. | 623/16 |
| 630625 | 12/1994 | European Pat. Off. | 623/17 |
| 4114657 | 4/1992 | Japan | 623/16 |
| 1645 | 5/1982 | WIPO | 606/71 |

*Primary Examiner*—Michael J. Milano

[57] ABSTRACT

A connector for segments of a modular surgical implant includes a first portion and a second portion. The first portion and second portion are configured to snap-fit together to mate and form a swivel coupling. A modular implant includes at least first and second segments which are connected by such a connector having first and second portions. The first portion is secured to the first segment and the second portion is secured to the second segment. The first portion and second portion are configured to mate and form a swivel such that the first segment and second segment are movable in multiplanar orientation relative to each other.

18 Claims, 6 Drawing Sheets

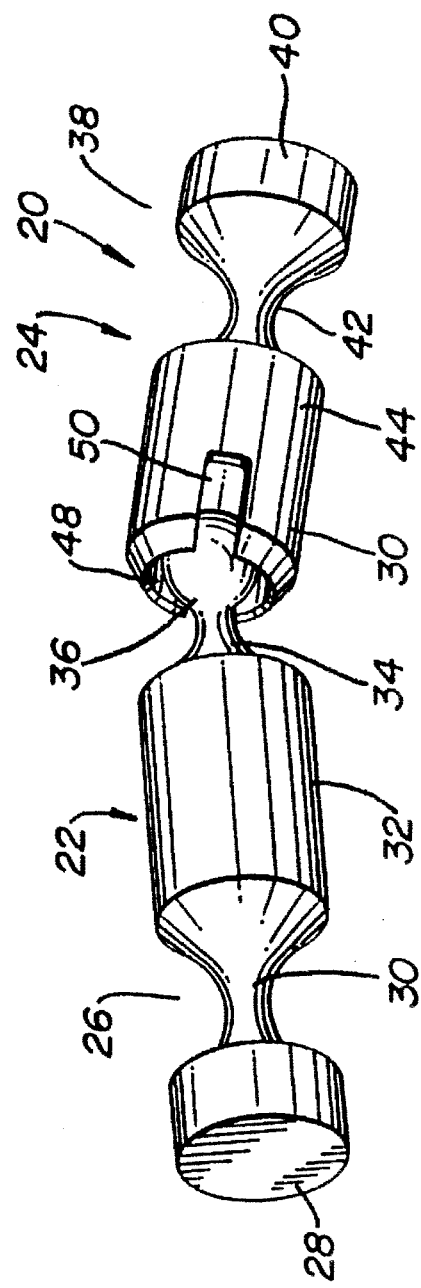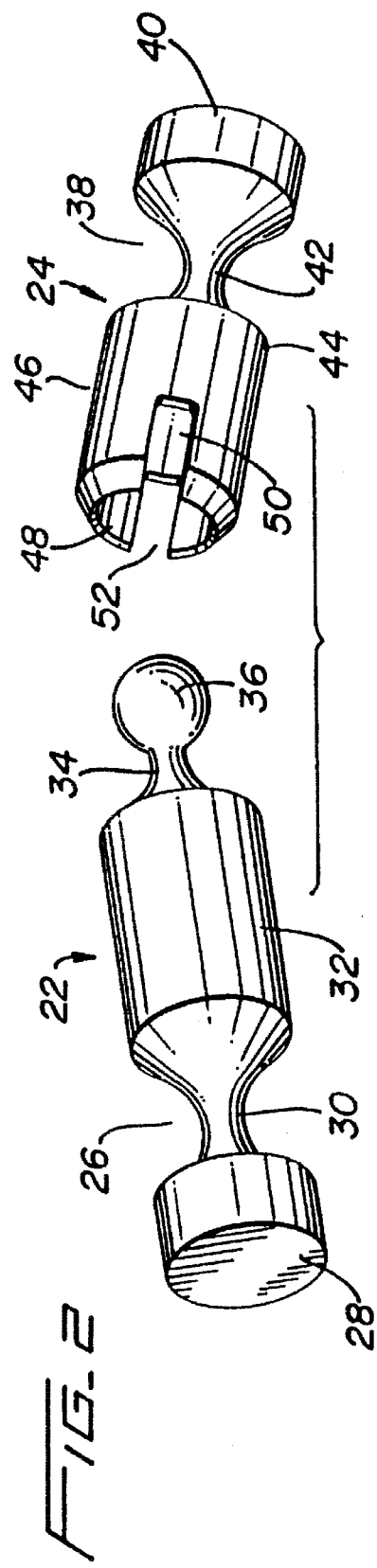
FIG. 1
FIG. 2

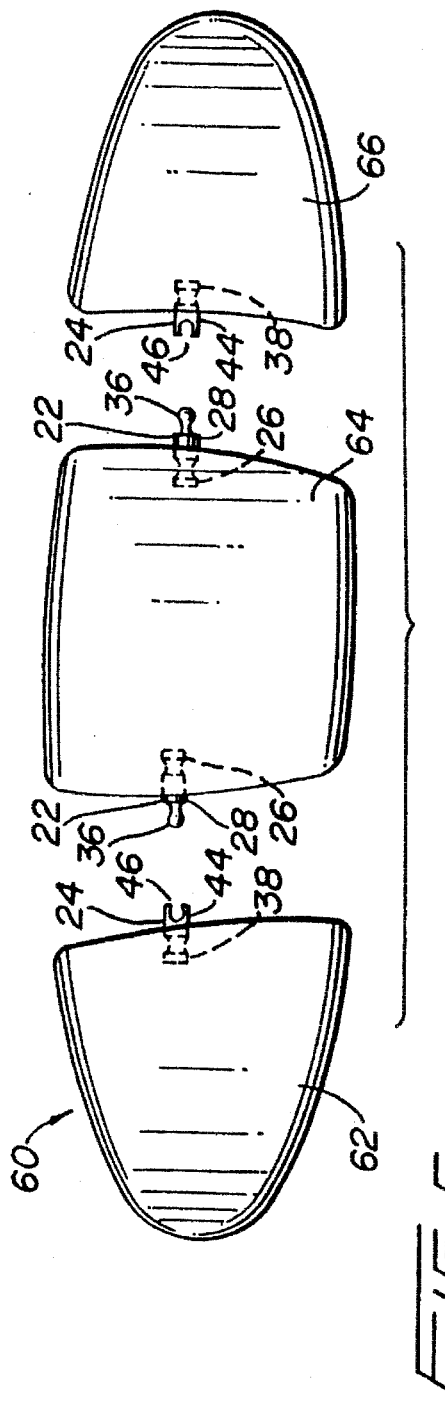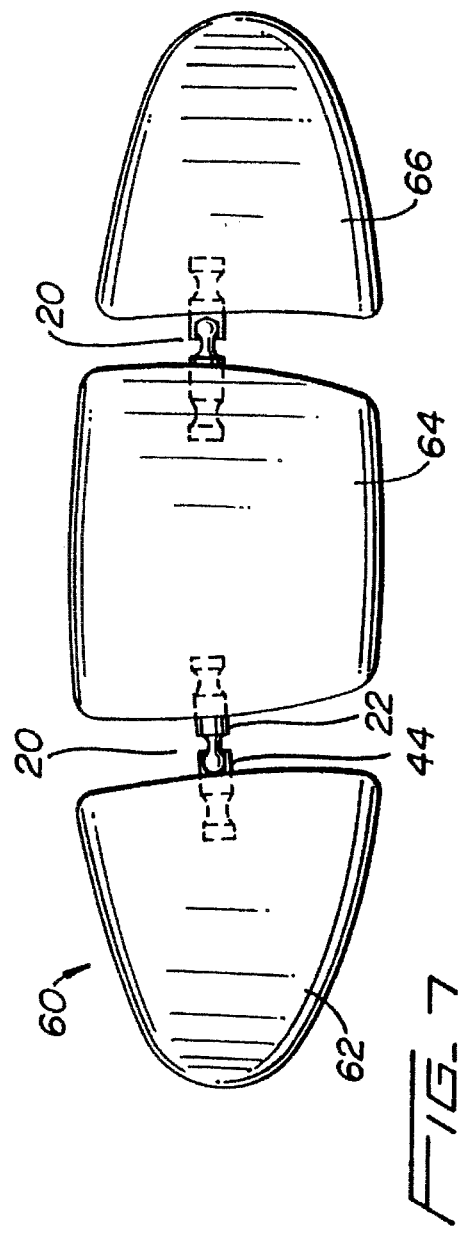

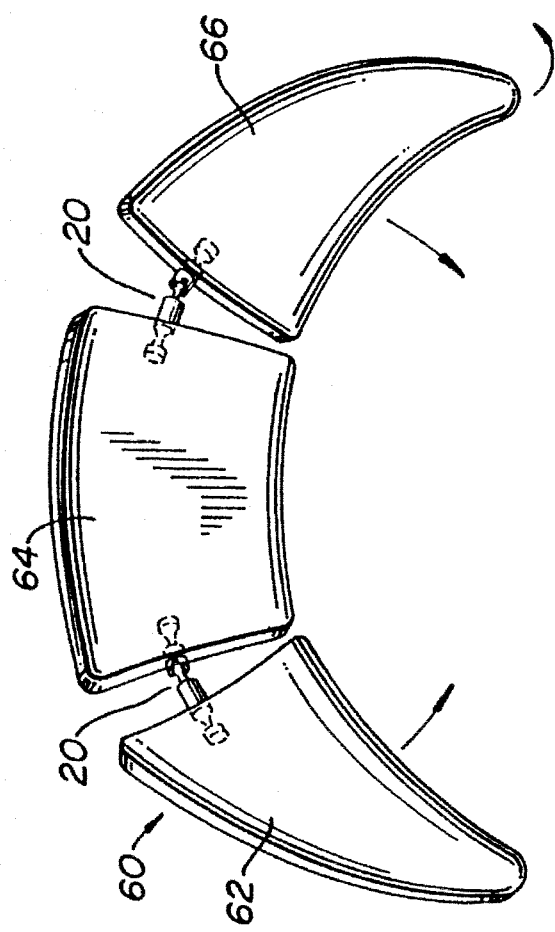
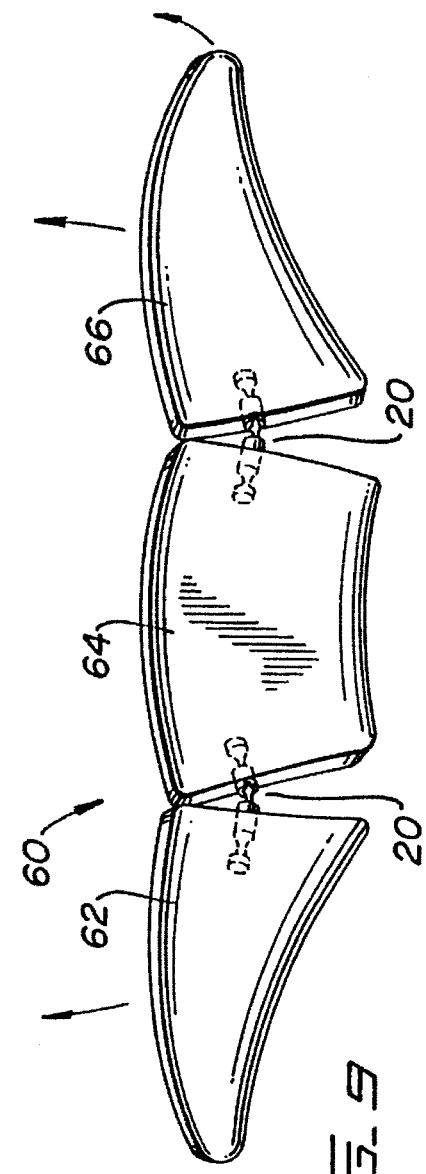

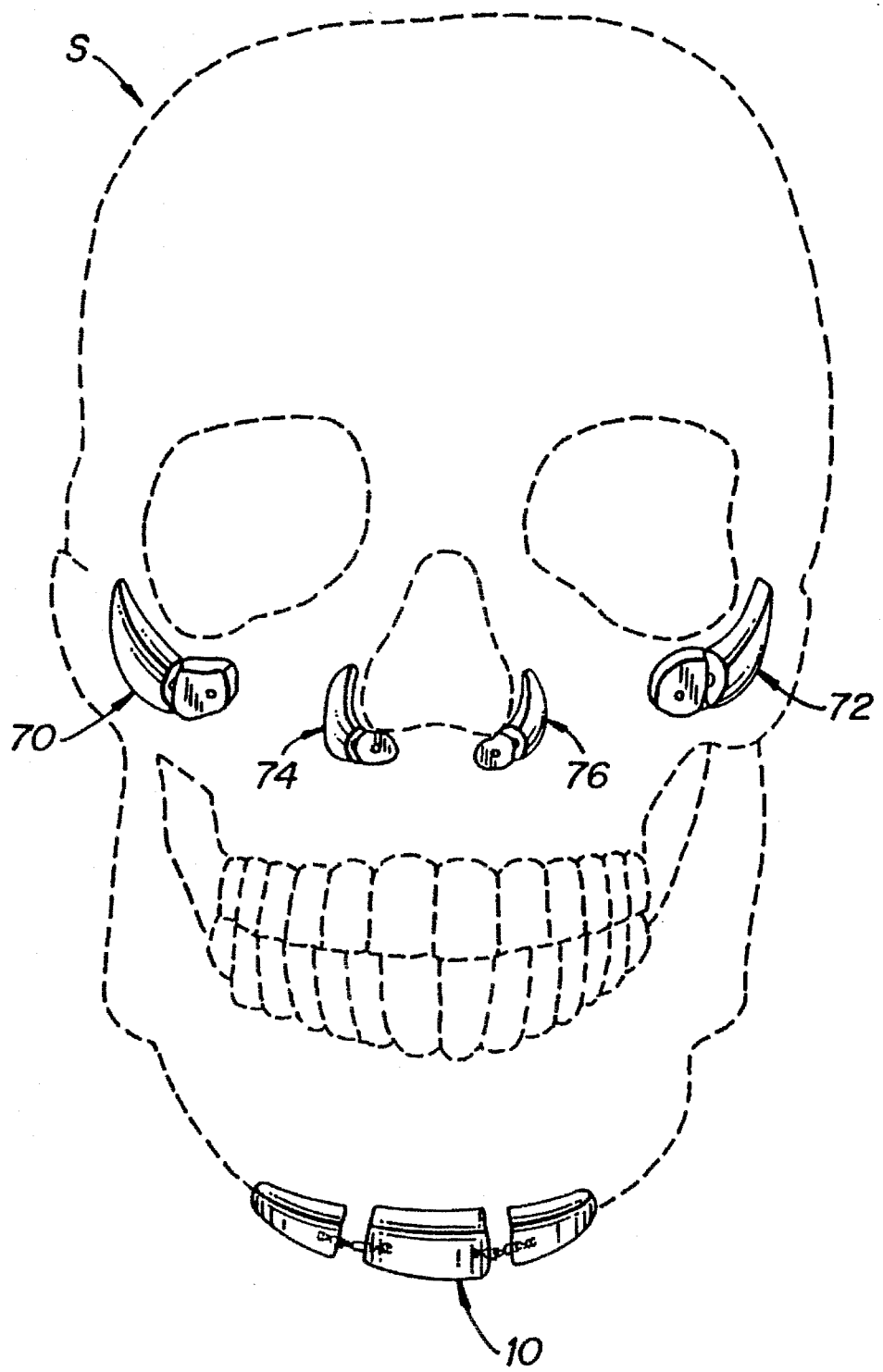
FIG_10

MODULAR SURGICAL IMPLANT

BACKGROUND

1. Technical Field

This disclosure relates to modular surgical implants and more particularly to modular implants for replacement, repair and/or augmentation of hard tissue.

2. Background of Related Art

Surgical implants are commonly used to replace, repair or augment hard tissue in the body of a patient and may be utilized when a body part is mutilated or damaged through trauma or disease. Surgical implants are also used as replacements or augmenters in cosmetic or plastic surgery.

Various materials are known in the art which can be used for making surgical implants. Examples of such materials are chromium-cobalt-molybdenum alloys, stainless steel, titanium alloys, ceramics and various polymers and polymer/ceramic composites. The materials used for surgical implants should be biocompatible, i.e., they must not adversely affect living tissue and the environment created by living tissue must not adversely affect the prosthetic.

In many cases, surgical implants must patch, replace or augment body parts such as bone which are rigid. Consequently, the implants are normally composed, at least in part, of rigid material. Additionally, the implants should approximate the size and shape of the body part being replaced or augmented. Since every patient is unique, a problem which often confronts practitioners is finding an implant with the requisite shape and proper fit, especially in instances where rigid implants are required.

In certain instances, a custom surgical implant is formed by making a mold of the body part of the individual patient and then deriving a custom surgical implant from the mold. A problem associated with this method is that it is time consuming due to the effort required in making the mold and then casting the implant. This also translates into higher costs for the patient. In other methods, a surgical implant is formed to the approximate size and shape of the body part and is subsequently carved or sculpted to fit the needs of the particular patient. The problem associated with achieving precise size and shape is compounded when the surgical implant is composed of rigid material, i.e., once the implant is formed it is time consuming and difficult to make adjustments to its size and shape. Any mistakes made in adjusting the configuration are difficult to correct and may require the fabrication of an entirely new implant.

Standardized preformed rigid implants have also been utilized. However, these standardized implants ordinarily do not account for differences in the bone or tissue structure among patients and may also have to be individually carved to the necessary shape to ensure a proper fit.

Additionally, in some surgical situations, the implants may be required to be inserted to the implant site via a tortuous or curved pathway. Insertion of a rigid implant along such pathway may damage surrounding tissue or may even cause fracture of the implant itself.

Therefore, the need exists for surgical implants, formed of a rigid material, which can accommodate the needs of individual patients without requiring each implant to be separately molded or individually sculpted to the required configuration. Such implants would simplify implantation and thus limit complicated time consuming and expensive surgical procedures. One such implant is disclosed in co-pending U.S. application Ser. No. 08/069,452 which discloses an implant of a plurality of spaced apart segments attached by flexible connecting members which can be bent to re-orient the segments so that the implant approximates the size and shape of the body part being treated.

SUMMARY

A connector for segments of a modular surgical implant is provided which includes a first portion and a second portion. The first portion has a first end and a second end; the first end is configured to be secured to one segment of a surgical implant, the second end having a first engaging structure to mate with a corresponding engaging structure on the second portion. The second portion of the connector has a first end and a second end; the first end is configured to be secured to another segment of the modular surgical implant, the second end incorporating the second engaging structure which is configured to mate with the first engaging structure of the first portion to form a snap-fit swivel coupling.

A modular surgical implant is provided which includes at least a first segment and a second segment. The first segment is connected to the second segment by a connector having a first portion and a second portion. The first portion is secured to the first segment and the second portion is secured to the second segment. The first portion and the second portion are dimensioned and configured to mate and form a swivel such that the first segment and second segment are movable in multiplanar orientation relative to each other.

A method of implanting a surgical implant is provided which includes providing first and second segments of a modular surgical implant, the first segment having a first portion of a connector secured thereto and the second segment having a second portion of a connector secured thereto. The first portion includes an engaging structure for mating with a corresponding engaging structure on the second portion to form a snap fit swivel coupling. The first segment and the second segment are inserted into a patient. The first segment and the second segment are combined by snap-fitting the engaging structure of the first portion to the corresponding engaging structure of the second portion. The modular surgical implant is shaped to a desired configuration by swiveling the first segment and second segment in relation to each other. When a desired configuration is achieved, the modular surgical implant is adhered to underlying bone.

BRIEF DESCRIPTION OF THE DRAWINGS

FIG. 1 is a perspective view of a connector for a modular surgical implant.

FIG. 2 is a perspective view of component portions of the connector shown in FIG. 1.

FIG. 6 is a front view of three separate segments of a modular surgical implant.

FIG. 7 illustrates three connected segments of the modular surgical implant shown separated in FIG. 6.

FIGS. 8 and 9 are bottom perspective views of the modular surgical implant shown in FIG. 7 with the segments re-oriented in the direction of the arrows.

FIG. 10 is a front view of a human skull showing anatomical positioning of a modular surgical chin implant, a modular surgical malar implant and a modular surgical paranasal implant.

DETAILED DESCRIPTION OF PREFERRED EMBODIMENTS

A connector for segments of a modular surgical implant and modular surgical implants incorporating the connector described herein allow standardized modular implant segments of various sizes and shapes to be interchanged and oriented by virtue of a swiveling snap-fit coupling. As a result, modular surgical implants can be tailored to the needs of individual patients by mixing and matching preformed stock modular segments. Use of such a modular implant allows a surgeon to decrease the size of incisions made during surgery since each modular segment can be separately inserted into the target area and then be assembled in situ. This is contrasted with a non-modular one piece implant which may require a larger incision to allow insertion of the entire full sized implant. The ability of the swiveling snap-fit coupling to provide multi-planar orientation of the modular segments allows each segment to be placed and angled as appropriate over underlying bone and the shape of the resulting prosthetic to be varied as desired.

Figure 3:
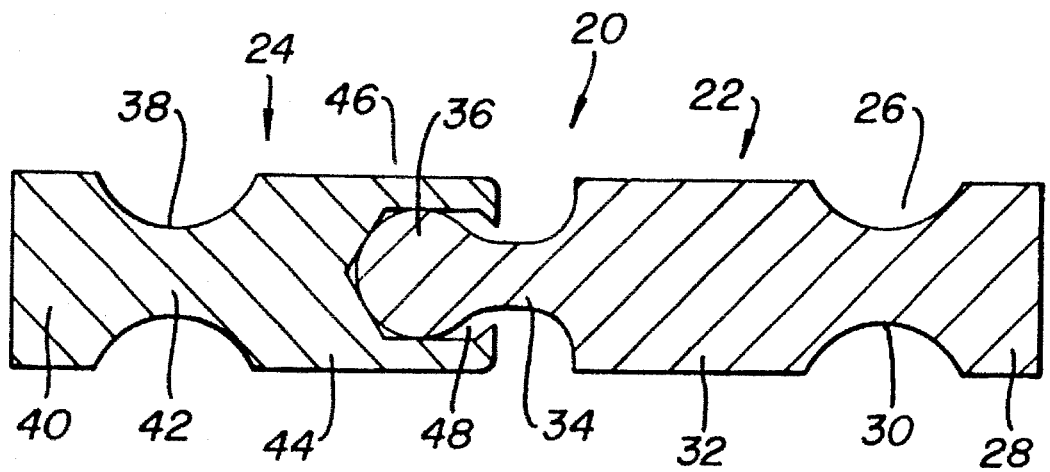
FIG. 3 is a cross-sectional side view of a connector for a modular surgical implant.
Figure 4:
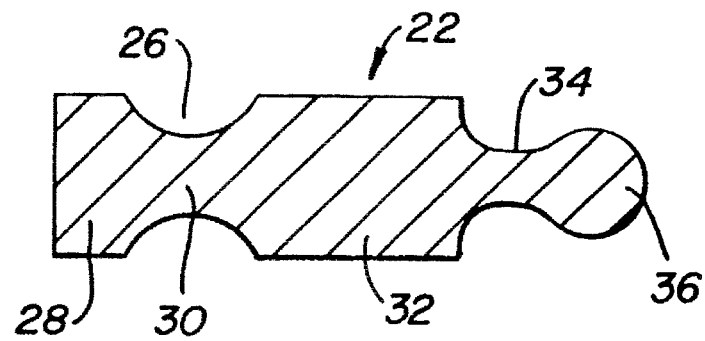
FIG. 4 is a cross-sectional side view of one portion of the connector shown in FIG. 3.

An assembled connector 20 is illustrated in FIGS. 1 and 3. The connector 20 includes a first portion 22 and a second portion 24. The first portion 22, shown separately in FIGS. 2 and 4, includes a first end 26 which serves to anchor the first portion 22 into a segment of a modular surgical implant. The first end 26 includes a cylindrical base portion 28 attached to a proximal end of a stem portion 30. The stem portion 30 has a smaller circumference than the base portion 28. A distal end of the stem portion 30 is connected to a proximal end of a cylindrical body portion 32. The distal end of the body portion 32 is connected by a neck 34 to a bulb-shaped head portion 36 that make up a first engaging structure which, as described below, mates with a second engaging structure on the second portion 24.

The first end 26 is configured to anchor the first portion 22 into a modular segment of a surgical implant. Such configuration, as illustrated, can be described as a spool-shaped. The base portion 28, stem portion 30, and body portion 32 cooperate to stabilize the first portion 22 of the connector 20 when it is mounted to a modular segment. The stem portion 30 provides an area for the material making up the segment to flow into and be retained, and upon hardening and/or bonding, prevents the first portion 22 from sliding out of the segment. The base portion 28 and body portion 32 stabilize the first portion 22 by cooperating to prevent radial displacement of the first portion 22.

Figure 5:
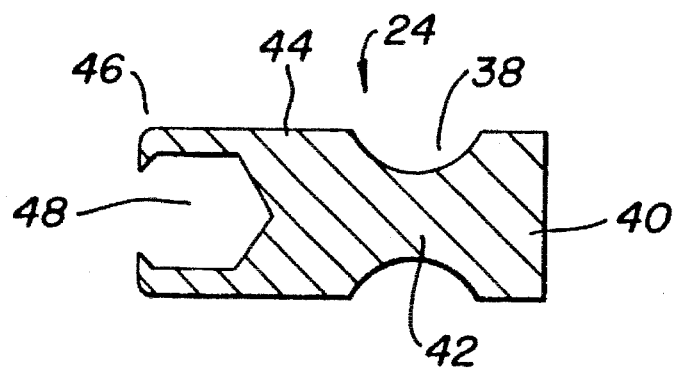
FIG. 5 is a cross-sectional side view of a second portion of the connector shown in FIG. 3.

The second portion 24 of the connector 20, shown separately in FIGS. 2 and 5, includes a first end 38 which, in a manner similar to the first end of the first portion, serves to anchor the second portion 24 into another segment of a modular surgical implant. The first end 38 includes a cylindrical base portion 40 attached to a proximal end of a stem portion 42. The stem portion 42 has a smaller circumference than the base portion 40. A distal end of the stem portion 42 is connected to a proximal end of a cylindrical body portion 44.

The first end 38 of the second portion 24 is configured to anchor the second portion into a modular segment of a surgical implant. Such configuration, as illustrated, can also be described as spool shaped. The base portion 40, stem portion 42, and body portion 44 cooperate to stabilize the second portion 24 when it is mounted to a modular segment. The stem portion 42 provides an area for the material making up the segment to flow into and be retained, and upon hardening or bonding, prevents the second portion 24 from sliding out of the segment. The base portion 40 and body portion 44 stabilize the second portion 24 by cooperating to prevent radial displacement of the second portion 24.

The second end 46 of the second portion 24 incorporates a second engaging structure for mating with the first engaging structure of the first portion 22 to for a snap-fit swivel coupling. The second end 46 of the second portion 24 includes a socket 48 having expansion slots 50 and 52. The open end or rim of the socket 48 is crimped radically inward and the socket 48 is configured to receive and retain the bulb-shaped head 36 of the first portion 22. When the first portion 22 is mated with the second portion 24, the head is pushed through the crimped opening and into the socket 48. The expansion slots 50 and 52 allow the socket walls to move outwardly as the head 36 pushes the crimped opening apart. As the widest portion of the head moves past the crimped portion, the opening of the socket 48 snaps back to its original diameter and thus retains the head 36. In a preferred embodiment, the head 36 fits snugly in the socket 48, but is free to swivel around within the socket. A snug fit provides some resistance to frictionless movement and unwanted further movement of the connector 20 once a desired orientation of the first portion 22 and second portion 24 is achieved. The only fixed constraint to swiveling occurs when the neck 34 contacts the walls of the socket 48. Thus, swiveling includes and allows a 360° range of rotation over a multiplanar range.

The connector 20 can be made of a variety of materials. Optimum materials are biocompatable and sufficiently strong to withstand reasonable stress generated by snap-fitting the first portion 22 and second portion 24 together and reasonable stress associated with orienting segments of a modular surgical implant. Preferred materials are metals such as stainless steel and titanium. Polymeric materials such as derivatives of carbonates, terephthalates, olefins, amides and urethanes may be utilized. In the case of metals, the first portion 22 and second portion 24 may be cast molded, stamped or machined to achieve the appropriate shapes. The polymeric materials may also be cast molded, stamped or machined to the appropriate shapes. It is contemplated that any shaping method known to those with skill in the art may be utilized to fashion the connector 20.

The connector 20 allows a multiplicity of modular segments to be assembled for creation of custom implants out of mass produced stock. Maxillofacial implants are especially suited to application of the present disclosure. For example, modular chin implant 60, illustrated in FIGS. 6–9, is configured to treat the lateral (external) outerior (front) portion of the mandible as shown in FIG. 10. The chin implant 60 includes three modular segments: a first chin segment 62, a second chin segment 64, and a third chin segment 66. The second portion 24 is secured to the first chin segment 62, i.e., the first end 38 (shown in phantom) anchors the second portion 24 within the first chin segment 62. The body portion 44 of the second portion 24 extends outwardly from the first chin segment 62 where the second end 46 is open to connect to a first portion 22 (FIG. 6).

Two first portions 22 are secured to opposite sides of the second chin segment 64. In both cases, the first end 26 (shown in phantom) anchors the first portion 22 within the second chin segment 64. The body portions 32 of the first portions 22 extend outwardly from both sides of the second chin segment 64 where the head portions 36 project outwardly ready to engage with any suitable second portion 24. Another second portion 24 is secured to the third chin segment 66 in a manner similar to the second portion 24 secured to the first chin segment 62, i.e., the first end 38 contained within the third chin segment 66 and the second end 46 projecting outwardly for receiving the head 36 of a first engaging structure. The modular chin implant 60 is shown assembled in FIG. 7 with the first engaging structure of the first portion 22 mated with the second engaging structure of the second portion 24 to form a snap-fit swivel coupling.

In accordance with the operation of the connector 20, the modular segments 62, 64 and 66 can be oriented at any angle within the swiveling radius provided by the snap-fit swivel coupling to allow adjustment of the implant 60 to conform to a particular patient's bone structure. Thus, not only can various sized and shaped segments be interchanged, but the angles on which the segments of the implant intersect the underlying bone structure is variable. For example, to accommodate a chin having a smaller radius of curvature, segments 62 and 66 can be bent inwardly in relation to chin segment 64, as shown in the direction of arrows to the configuration shown in FIG. 8. The connectors 20 allow the segments to be configured so that any of the segments 62, 64 and/or 66 can be moved inwardly, outwardly, upwardly, downwardly, diagonally or in any direction relative to each other. See FIG. 9. Moreover, the swivel coupling allows the segments to be rotated coaxially in relation to any adjacent segments.

Figure 11:
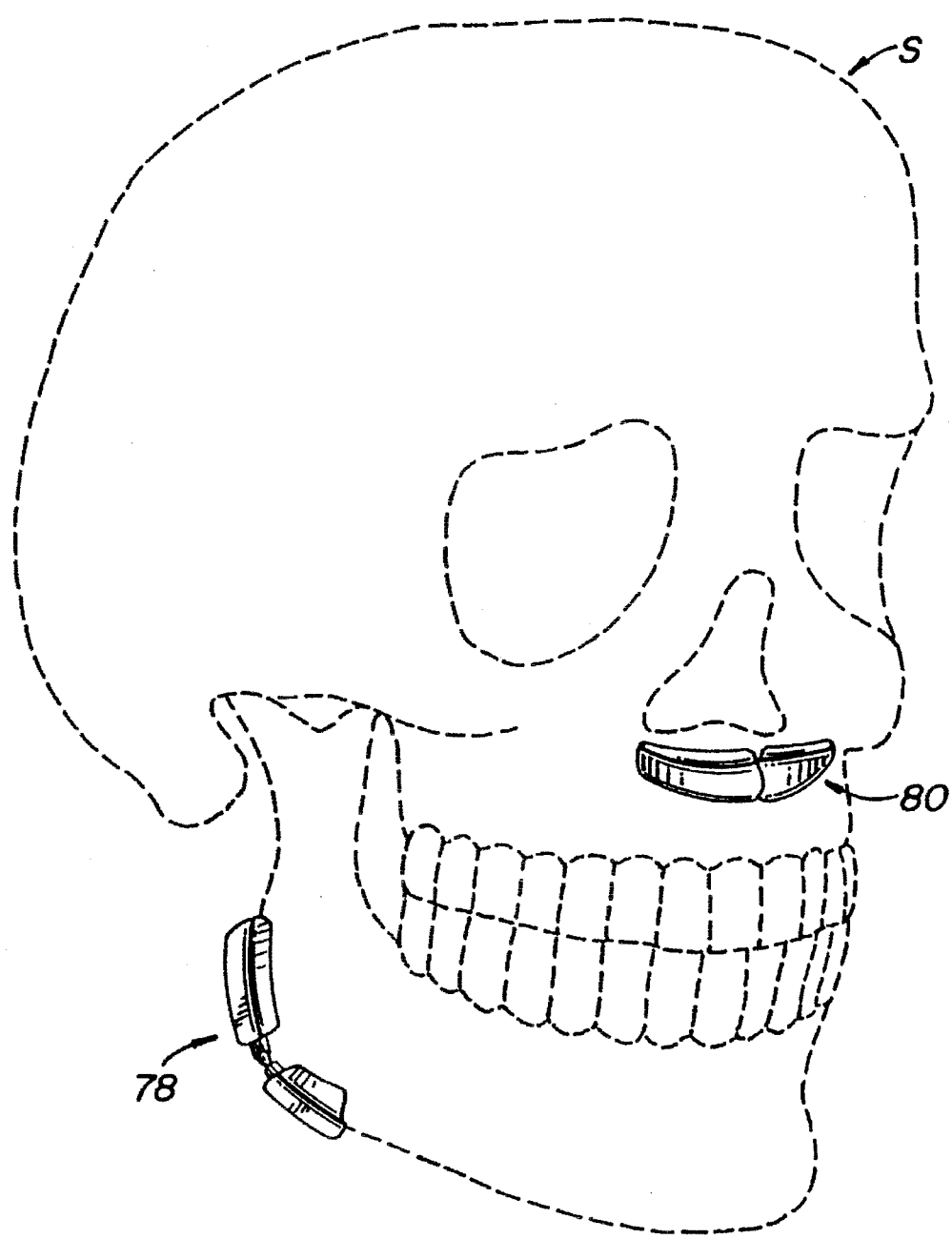
FIG. 11 is a front perspective view of a human skull showing anatomical positioning of a modular surgical premaxillary implant and a modular surgical left-side gonial implant.

The connector 20 described herein may be used to connect the segments of any maxillofacial modular surgical implant including chin, malar, paranasal, gonial angle and premaxillary implants. Such implants are illustrated in FIGS. 10 and 11 attached to a human skull S. Right and left side modular malar implants 70 and 72 are positioned to augment or replace the lateral portion of the right and left zygomatic bones, respectively, as shown in FIG. 10. Right and left side modular paranasal implants 74 and 76, are positioned to treat the lateral portion of the maxilla along the left and right sides of the inferior nasal concha. The modular chin implant 60 is also shown mounted to the chin bone in FIG. 10. A modular left side gonial implant 78 and a modular premaxillary implant are shown in position against the skull S in FIG. 11.

It is contemplated that the connector 20 described herein is not limited to use in connecting modular segments of chin, malar, paranasal, genial angle or premaxillary implants, but may be used in modular implants for any part of the body.

The modular segments of the implant may be made of any biocompatable material suitable for withstanding any reasonable stress to which the segments may be subjected during or after implantation. The segments should be strong and durable and, in certain cases, can be made to effectively induce the growth of tissue or bone in or around its location. In a preferred embodiment, a porous structure of a polymeric composite such as polymethylmethacrylate (PMMA) is coated with a polymeric hydrophilic material, such as polyhydroxyethylmethacrylate (PHEMA). Various materials which render the segments opaque to X-rays may also be incorporated, e.g., barium sulfate. These materials and processes for making these materials are disclosed in U.S. Pat. Nos. 4,547,390, 4,547,327, and 4,728,570, herein incorporated by reference. It is contemplated, however, that any other suitable prosthetic material which is known to those with skill in the art such as dense or porous ceramics, polymer/ceramic composites or metals can be used in accordance with the present disclosure. The materials can also include, for example, resorbable polymeric material such as polymers or copolymers of glycolide, lactide, and/or polydioxanone.

In forming the modular implants, the distance between adjacent segments may be varied to suit different applications by increasing or decreasing the length of the connector 20. A greater distance between segments allows more of an angle to be achieved between adjacent segments. The distance between segments preferably ranges from 0.005 inches to 0.25 inches; however larger or smaller distances are within the scope of the present invention. In situations where the segments are spaced far apart, the void between segments may be filled with a bone substitute such as granular HTR® polymer, a trademark of United States Surgical Corporation. Moreover, a different number of segments than illustrated herein can be utilized (e.g. a larger number of segments for increasing flexibility) and the shape and configuration of the individual segments (e.g. the location of the segmentation) can vary depending on its use.

Although the chin implant 60, the paranasal implants 74 and 76, the malar implants 70 and 72, the gonial angle implant 78 and premaxillary implant 80 are illustrated as having longitudinal gaps between the segments, it is contemplated that the gaps can be latitudinal or diagonal as well. Indeed, latitudinal, longitudinal and diagonal gaps may be incorporated into the same modular implant to allow segments to be positioned at all sorts of appropriate angles and directions. It is also contemplated that more than one connector can be used to traverse the gap at different points between segments.

One with ordinary skill in the art may use any appropriate method or means that are known for attaching the modular surgical implants described herein to the facial bones of the skull. For example, metal or plastics screws can be inserted through one or more of the segments of the implant material to secure the implant to the body.

It will be understood that various modifications may be made to the embodiments disclosed herein. For example, the connector 20 is illustrated as being mostly cylindrical, but it is contemplated that it may have a rectangular, polygonal, square, ellipsoid, etc. cross-sectional aspect. The head is shown to be bulb-shaped, but may also have other configurations such as polygonal and the like. The anchoring portion of the connector is described as spool-shaped, but may also have other irregular shapes as long as the anchor function is achieved. If more than one connector is placed in a segment of a modular surgical implant, e.g., as illustrated in FIGS. 6–10 (segment 64), second portions may be used instead of first portions or one side of the segment may incorporate a first portion while the other side may incorporate a second portion, as long as corresponding engaging structures are made available for mating with the next adjacent segment. Therefore, the above description should not be construed as limiting, but merely exemplifications of preferred embodiments. Those skilled in the art will envision other modifications within the scope and spirit of the claims appended hereto.

What is claimed is:

1. A biocompatible connector for segments of a modular surgical implant comprising a first portion and a second portion, the first portion having first and second ends, the first end configured to be secured into one segment of a modular surgical implant, the second end having a first engaging structure to mate with a corresponding second engaging structure on the second portion, the second portion having first and second ends, the first end configured to be secured into another segment of the modular surgical implant, the second end incorporating the second engaging structure which is configured to mate with the first engaging structure of the first portion to form a snap-fit swivel coupling.

2. A connector for segments of a modular surgical implant according to claim 1 wherein the first engaging structure is a bulb-shaped member and the second engaging structure is a socket configured to receive and retain the bulb-shaped member.

3. A connector for segment of a modular surgical implant according to claim 1 wherein the first end of the first portion is spool shaped.

4. A connector for segments of a modular surgical implant according to claim 1 wherein the first end of the second portion is spool shaped.

5. A connector for segments of a modular surgical implant o according to claim 2 wherein the first portion and the second portion mate such that the bulb-shaped member and the socket cooperate to allow the bulb-shaped member to swivel within the socket.

6. A modular surgical implant comprising at least a first segment and a second segment, the first segment being connected to the second segment by a connector having a first portion and a second portion, the first portion being secured into the first segment and the second portion being secured into the second segment, the first portion and the second portion dimensioned and configured to mate and form a swivel such that the first segment and second segment are movable in multiplanar orientation relative to each other.

7. A modular surgical implant according to claim 6 wherein the first portion includes a first engaging structure which is bulb-shaped, and the second portion includes a second engaging structure which is a socket dimensioned and configured to receive and retain the bulb-shaped first engaging structure.

8. A modular surgical implant according to claim 6 wherein the modular surgical implant is dimensioned and configured to conform to at least a portion of maxillofacial bone.

9. A modular surgical implant according to claim 6 wherein the first portion has a spool shaped anchor which engages and secures the first segment to the first portion.

10. A modular surgical implant according to claim 6 wherein the second portion has a spool shaped anchor which engages and secures the second segment to the second portion.

11. A modular surgical implant according to claim 6 wherein the first and second segments are made of a material selected from the group consisting of polymer, polymer/ceramic composite, ceramic and metal.

12. A modular surgical implant according to claim 6 wherein the first and second segments are at least partially bioabsorable.

13. A modular surgical implant according to claim 7 wherein the socket includes at least one expansion slot.

14. A method of implanting a surgical implant comprising:
providing first and second segments of a modular surgical implant, the first segment having a first portion of a connector secured thereto, the second portion having a second portion of the connector secured thereto, the first portion having an engaging structure for mating with a corresponding engaging structure of the second portion to form a snap-fit swivel coupling;
inserting the first segment into a patient;
inserting the second segment into a patient;
combining the first segment with the second segment by snap-fitting the engaging structure of the first portion to the corresponding engaging structure of the second portion;
shaping the modular surgical implant to a desired configuration by swiveling the first segment in relation to the second segment; and
adhering the modular surgical implant to underlying bone.

15. A biocompatible connector for segments of a modular surgical implant comprising a first portion and a second portion, the first portion having first and second ends, the first end configured to be secured to one segment of a modular surgical implant, the second end having a male first engaging structure to mate with a corresponding female second engaging structure on the second portion, the femme engaging structure including at least one expansion slot, the second portion having first and second ends, the first end configured to be secured to another segment of the modular surgical implant, the second end incorporating the second engaging structure which is configured to a mate with the first engaging structure of the first portion to form a snap-fit swivel coupling.

16. A connector for segments of a modular surgical implant according to claim 15 wherein the first engaging structure is a bulb-shaped member and the second engaging structure is a socket configured to receive and retain the bulb-shaped member.

17. A connector for segment of a modular surgical implant according to claim 15 wherein the first end of the first portion is spool shaped.

18. A connector for segments of a modular surgical implant according to claim 15 wherein the first end of the second portion is spool shaped.

* * * * *